(12) United States Patent
Quinn

(10) Patent No.: US 12,714,582 B2
(45) Date of Patent: Aug. 25, 2026

(54) BIFURCATED SIDE-ACCESS INTRAVASCULAR STENT GRAFT

(71) Applicant: W. L. Gore & Associates, Inc., Newark, DE (US)

(72) Inventor: Stephen F. Quinn, Eugene, OR (US)

(73) Assignee: W. L. Gore & Associates, Inc., Newark, DE (US)

( * ) Notice: Subject to any disclaimer, the term of this patent is extended or adjusted under 35 U.S.C. 154(b) by 552 days.

(21) Appl. No.: 17/482,120

(22) Filed: Sep. 22, 2021

(65) Prior Publication Data

US 2022/0008230 A1 Jan. 13, 2022

Related U.S. Application Data

(60) Division of application No. 17/100,345, filed on Nov. 20, 2020, now abandoned, which is a continuation of
(Continued)

(51) Int. Cl.
*A61F 2/07* (2013.01)
*A61F 2/82* (2013.01)
(Continued)

(52) U.S. Cl.
CPC .................. *A61F 2/82* (2013.01); *A61F 2/07* (2013.01); *A61F 2/856* (2013.01);
(Continued)

(58) Field of Classification Search
CPC ...... A61F 2/07; A61F 2/856; A61F 2002/061; A61F 2230/005; A61F 2230/0095
(Continued)

(56) References Cited

U.S. PATENT DOCUMENTS 3,657,744 A * 4/1972 Ersek ........................ A61F 2/07 623/902
5,197,976 A 3/1993 Herweck et al.
(Continued)

FOREIGN PATENT DOCUMENTS

JP 2000-279532 A 10/2000
WO WO-0045741 A1 * 8/2000 ............... A61F 2/07
(Continued)

*Primary Examiner* — Brian E Pellegrino

(57) ABSTRACT

A bifurcated intravascular stent graft comprises primary stent segments and a primary graft sleeve, forming a main fluid channel and having a side opening therethrough. An external graft channel formed on the primary graft sleeve has a first end communicating with the side opening and an open second end outside the primary graft sleeve, thereby providing a branch flow channel from the main channel out through the side opening and external graft channel. The primary stent segments and graft sleeve engage an endoluminal surface of a main vessel and form substantially fluid-tight seals. The stent graft further comprises a secondary stent graft, which may be positioned partially within the external graft channel, through the open second end thereof, and partially within a branch vessel. The secondary stent graft engages the inner surface of the external graft channel and the endoluminal surface of the branch vessel, thereby forming substantially fluid-tight seals.

20 Claims, 12 Drawing Sheets

Related U.S. Application Data application No. 13/906,247, filed on May 30, 2013, now abandoned, which is a continuation of application No. 11/971,426, filed on Jan. 9, 2008, now Pat. No. 8,556,961.

(51) Int. Cl.

| | |
|---|---|
| ***A61F 2/856*** | (2013.01) |
| *A61F 2/06* | (2013.01) |
| *A61F 2/89* | (2013.01) |

(52) U.S. Cl.

CPC ... *A61F 2002/061* (2013.01); *A61F 2002/067* (2013.01); *A61F 2002/075* (2013.01); *A61F 2/89* (2013.01); *A61F 2220/0075* (2013.01)

(58) Field of Classification Search

USPC ........................................................ 623/1.35

See application file for complete search history.

(56) References Cited

U.S. PATENT DOCUMENTS

| | | | | |
|---|---|---|---|---|
| 5,628,787 | A | 5/1997 | Mayer | |
| 5,755,773 | A | 5/1998 | Evans et al. | |
| 5,755,778 | A | 5/1998 | Kleshinski | |
| 5,788,681 | A | 8/1998 | Weaver et al. | |
| 5,824,040 | A | 10/1998 | Cox et al. | |
| 5,855,598 | A | 1/1999 | Pinchuk | |
| 5,877,263 | A | 3/1999 | Patnaik et al. | |
| 5,893,887 | A | 4/1999 | Jayaraman | |
| 5,906,641 | A | 5/1999 | Thompson et al. | |
| 5,957,974 | A | 9/1999 | Thompson et al. | |
| 5,972,023 | A | 10/1999 | Tanner et al. | |
| 5,984,955 | A | 11/1999 | Wisselink | |
| 5,993,481 | A | 11/1999 | Marcade et al. | |
| 6,048,360 | A | 4/2000 | Khosravi et al. | |
| 6,090,136 | A | 7/2000 | Mcdonald et al. | |
| 6,093,203 | A | 7/2000 | Uflacker | |
| 6,129,756 | A | 10/2000 | Kugler et al. | |
| 6,210,429 | B1 | 4/2001 | Vardi et al. | |
| 6,334,867 | B1 | 1/2002 | Anson | |
| 6,344,056 | B1 | 2/2002 | Dehdashtian | |
| 6,355,056 | B1 | 3/2002 | Pinheiro | |
| 6,468,301 | B1 | 10/2002 | Amplatz et al. | |
| 6,645,242 | B1 | 11/2003 | Quinn | |
| 6,811,566 | B1 | 11/2004 | Penn et al. | |
| 6,814,752 | B1 | 11/2004 | Chuter | |
| 6,949,121 | B1 | 9/2005 | Laguna | |
| 7,828,837 | B2 | 11/2010 | Khoury | |
| 8,556,961 | B2 | 10/2013 | Quinn | |
| 8,808,358 | B2 | 8/2014 | Khoury | |
| 8,870,946 | B1 | 10/2014 | Quinn | |
| 9,597,209 | B2 | 3/2017 | Khoury | |
| 9,861,505 | B2 | 1/2018 | Khoury | |
| 2003/0040771 | A1 | 2/2003 | Hyodoh et al. | |
| 2003/0130720 | A1 | 7/2003 | Depalma et al. | |
| 2005/0059923 | A1 * | 3/2005 | Gamboa | A61F 2/86 604/9 |
| 2005/0131518 | A1 * | 6/2005 | Hartley | A61F 2/856 623/1.13 |
| 2006/0095118 | A1 * | 5/2006 | Hartley | A61F 2/856 623/1.35 |
| 2009/0043376 | A1 | 2/2009 | Hamer et al. | |
| 2013/0218259 | A1 | 8/2013 | Quinn | |
| 2013/0274857 | A1 | 10/2013 | Quinn | |
| 2021/0068992 | A1 | 3/2021 | Quinn | |

FOREIGN PATENT DOCUMENTS

| | | | | |
|---|---|---|---|---|
| WO | 01/74270 A2 | | 10/2001 | |
| WO | WO-2008021557 A1 | * | 2/2008 | A61F 2/07 |

* cited by examiner 100
250
230
200

240
200
220
260
230
100
9
100
230
8
4
4
200
200
200
6
6
200
250
7
7
250
260
5
5
240
9
8
240

200
280
290
235
260
210

200
215
280
260
215
235
220
215
200
215
280
235
220

200
280
215
250
235
260
220
215

230
230
210
200
235
270
200
280
215
215
235
220

240
210
200
235
290
280
260
200
235
250
215
215
200
235
220

240

100
230
250
200
200
302

320
240
340
220
300
15
230
100
100
230
200
200
300
302
13
13
300
302
14
14
320
340
250
340
250
200
200
240
15

240

200
235
215
215
302
220
280
215
310
340

200
215
235
302
320
215
340
220
280
215
230
210
200
235
290
200
330
310
280
320
302
302
235
215
340
302
215
200
235
240
220

200
290
280
285
235
260
210

200
215
260
280
215
285
235
220
215
235
280
200
18
18
220

200
215
280
215
250
235
260
220
215

230
210
19
19
200
235
270
290
200
285
260
280
21
21
250
235
22
22
215
215
235
200
20
20

220
240

280
270
280
270
280
270

270
280
270
284
280
284
280
270

280
270
280
270

200
290
280
235
282
210
260

200
200
215
282
235
220
260
280
200
280
235
220
282

200
200
282
215
235
200
220

200
235
215
220
280
215
310
302
340

200
235
215
220
280
215
302
320
340
315
34
34
230
210
200
235
200
290
330
310
280
32
32
320
302
302
235
340
33
33
302
315
215
215
200
235
240
220

100
200
230
252
262
292
262
262
220
252
292
240
200
123
200
340
320
302
230
300
100
220
302
240
200
300
340
320

BIFURCATED SIDE-ACCESS INTRAVASCULAR STENT GRAFT

CROSS-REFERENCE TO RELATED APPLICATIONS

This application is a Divisional of U.S. application Ser. No. 17/100,345, filed Nov. 20, 2020, which is a Continuation of U.S. application Ser. No. 13/906,247, filed May 30, 2013, which is a Continuation of U.S. application Ser. No. 11/971,426, filed Jan. 9, 2008, now U.S. Pat. No. 8,556,961, issued Oct. 15, 2013, the contents of which are hereby incorporated by reference in their entireties.

BACKGROUND

Field

The field of the present invention relates to intravascular stent grafts. In particular, a bifurcated side-access intravascular stent graft and methods for fabricating and deploying the same are described herein.

Discussion

In many instances of vascular disease, a damaged, weakened, and/or enlarged portion of a blood vessel must be protected from intravascular fluid pressure. Continued exposure to such fluid pressure may result in progression of damage to the affected area and/or vessel failure, accompanied by significant morbidity or even sudden death. A well-established technique for treating such vascular damage is the use of transluminally-deployed stent grafts.

Briefly, a stent graft comprises two major components, a stent and a graft. The stent (one or more) typically takes the form of a somewhat stiff tube-like structure inserted into an affected vessel and fixed in place. The stent may serve to maintain a patent vessel lumen, may serve as structural support for the vessel, and/or may serve as an attachment/seal for a graft. A graft typically takes the form of a flexible tube or sleeve which is at least somewhat fluid-tight (although varying degrees of permeability may be desirable for a variety of reasons). When secured within a vessel using stents (a single stent the length of the graft, a pair of stent segments at the ends of the graft, or multiple stent segments spaced along the length of the graft), the graft becomes a surrogate vessel-within-a-vessel, and bears the brunt of the intravascular fluid pressure. It has become common practice to bridge damaged vessel segment using a sufficiently long graft secured within the vessel with stent segments.

Complications arise, however, when vessel damage occurs near a vessel branch point. More elaborate, multi-component devices are required to both shield the damaged vessel portion while maintaining blood flow through the main and branch vessels. Such devices are described in the following patents and references cited therein. Each of the following patents is hereby incorporated by reference as if fully set forth herein: U.S. Pat. Nos. 5,906,641; 6,093,203; 5,855,598; 5,972,023; 6,129,756; 5,824,040; 5,628,787; and 5,957,974.

Many of the prior-art devices are suitable for vessel branches where the branch vessel leaves the main vessel at a relatively small angle (less than about 45°, or example). For larger branching angles (as large as about 90° or even up to about 180°, for example) many prior art devices are not suitable. Such large branching angles occur at several potentially important repair sites (particularly along the abdominal aorta, at the renal arteries, celiac artery, superior and inferior mesenteric arteries, for example). Another drawback common to many devices of the prior-art is the need for transluminal access through the branch vessel from a point distal of the repair site. In many instances such access is either impossible (celiac artery, mesenteric arteries, renal arteries) or extremely difficult and/or dangerous (carotid arteries). Still other previous devices do not provide a substantially fluid-tight seal with the branch vessel, thereby partially defeating the purpose of the stent graft (i.e., shielding the repaired portion of the main vessel and/or branch vessel from intravascular fluid pressure).

It is therefore desirable to provide a bifurcated side-access intravascular stent graft and methods for fabricating and deploying the same, wherein the stent graft may be deployed transluminally to repair vessels having large-angle branch vessels (ranging from about 0° up to about 180°, for example). It is therefore desirable to provide a bifurcated side-access intravascular stent graft and methods for fabricating and deploying the same, providing a substantially fluid-tight seal with the main vessel and the branch vessel. It is therefore desirable to provide a bifurcated side-access intravascular stent graft and methods for fabricating and deploying the same, wherein the stent graft may be deployed transluminally without distal access through the branch vessel. It is therefore desirable to provide a bifurcated side-access intravascular stent graft and methods for fabricating and deploying the same, wherein the stent graft may be readily and accurately positioned relative to the branch vessel.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIG. 37 shows a front view of a primary stent graft according to the present invention.

FIG. 41 shows a longitudinal-sectional view of a primary stent graft according to the present invention.

Figures 1, 2, 3:
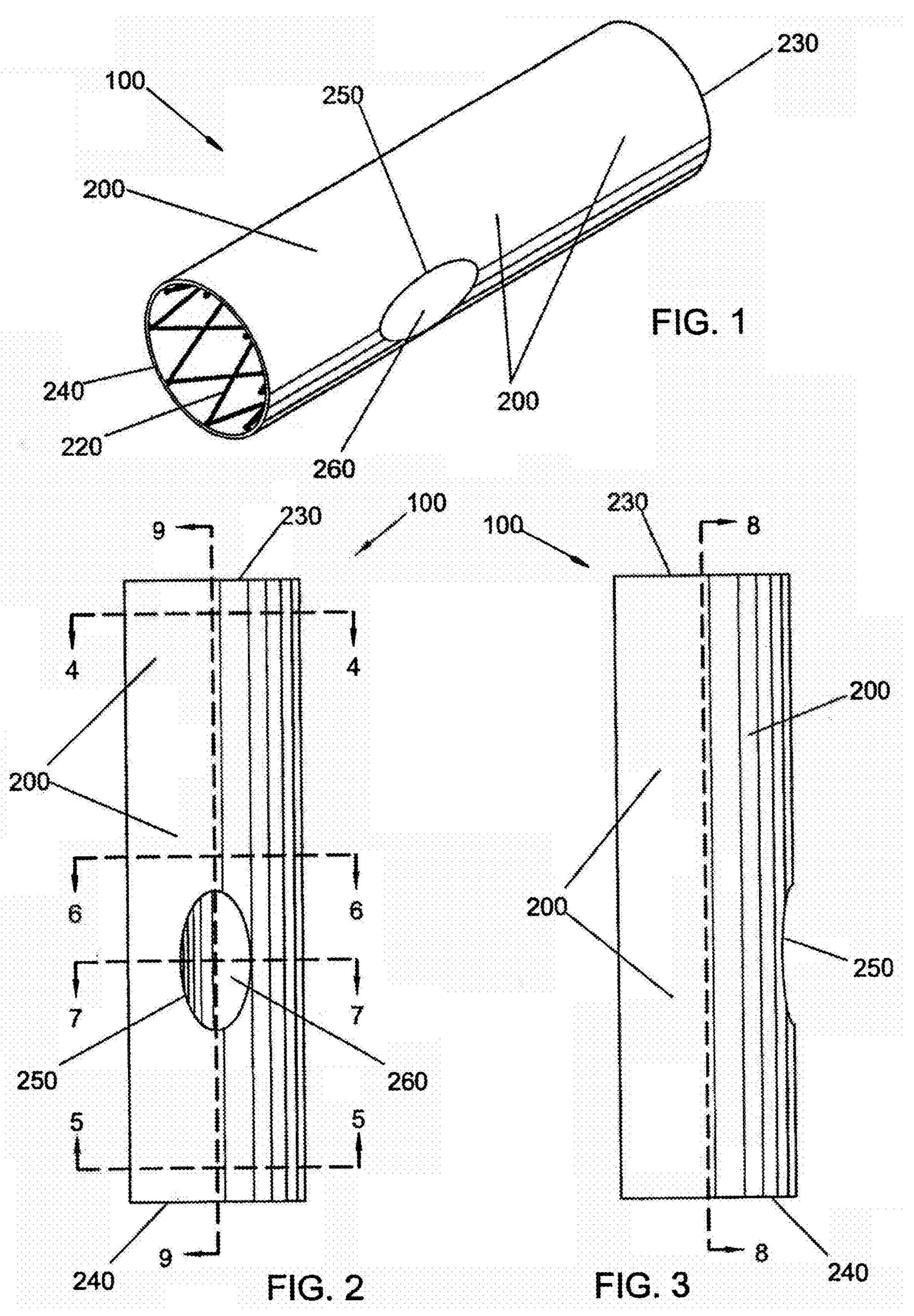
FIG. 1 shows an isometric view of a primary stent graft according to the present invention.
FIG. 2 shows a front view of a primary stent graft according to the present invention.
FIG. 3 shows a side view of a primary stent graft according to the present invention.
Figures 4, 5, 6, 7, 8, 9:
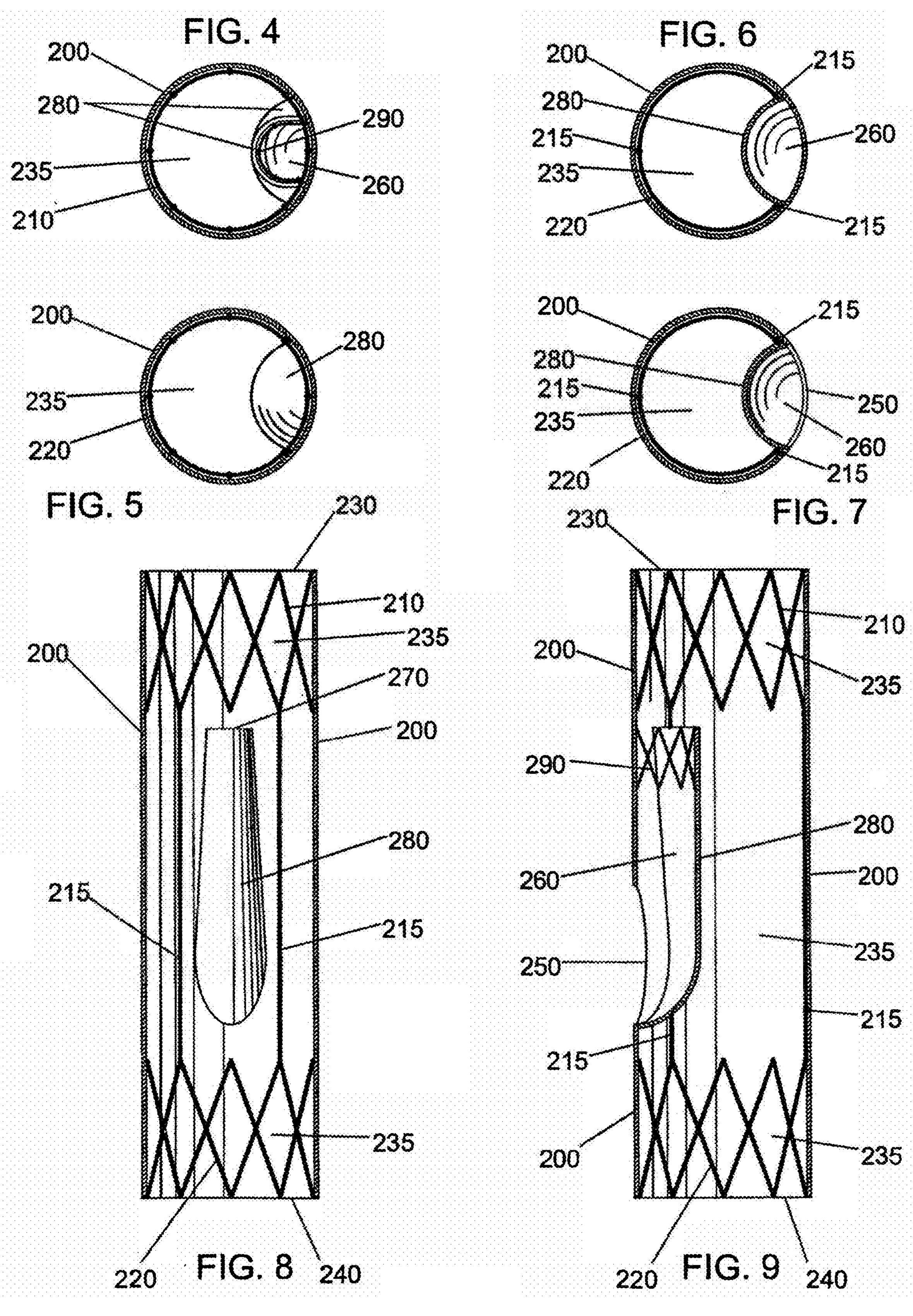
FIG. 4 shows a transverse-sectional view of a primary stent graft according to the present invention.
FIG. 5 shows a transverse-sectional view of a primary stent graft according to the present invention.
FIG. 6 shows a transverse-sectional view of a primary stent graft according to the present invention.
FIG. 7 shows a transverse-sectional view of a primary stent graft according to the present invention.
FIG. 8 shows a longitudinal-sectional view of a primary stent graft according to the present invention.
FIG. 9 shows a longitudinal-sectional view of a primary stent graft according to the present invention.
Figures 10, 11, 12:
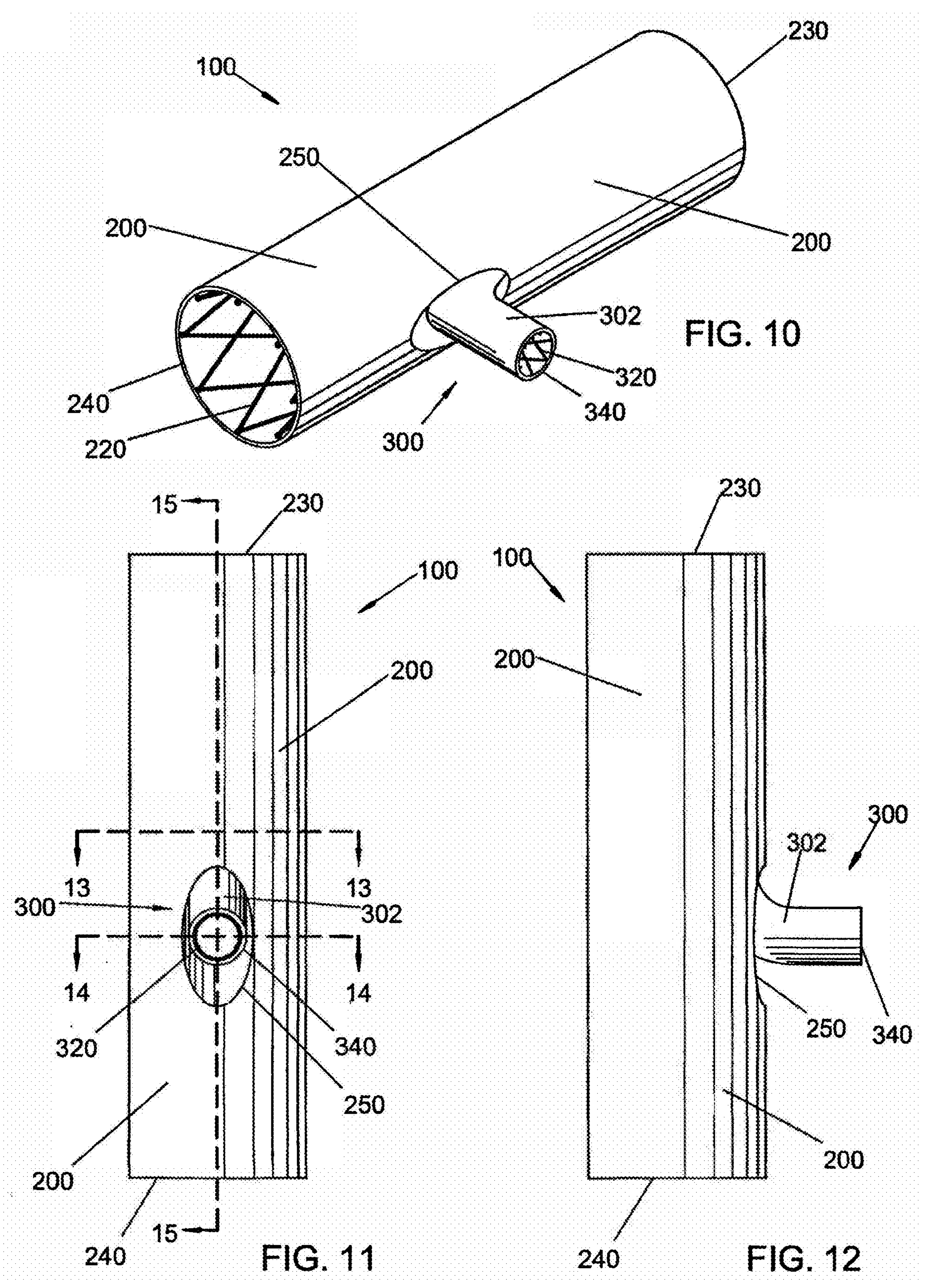
FIG. 10 shows an isometric view of a bifurcated stent graft according to the present invention.
FIG. 11 shows a front view of a bifurcated stent graft according to the present invention.
FIG. 12 shows a side view of a bifurcated stent graft according to the present invention.
Figures 13, 14, 15:
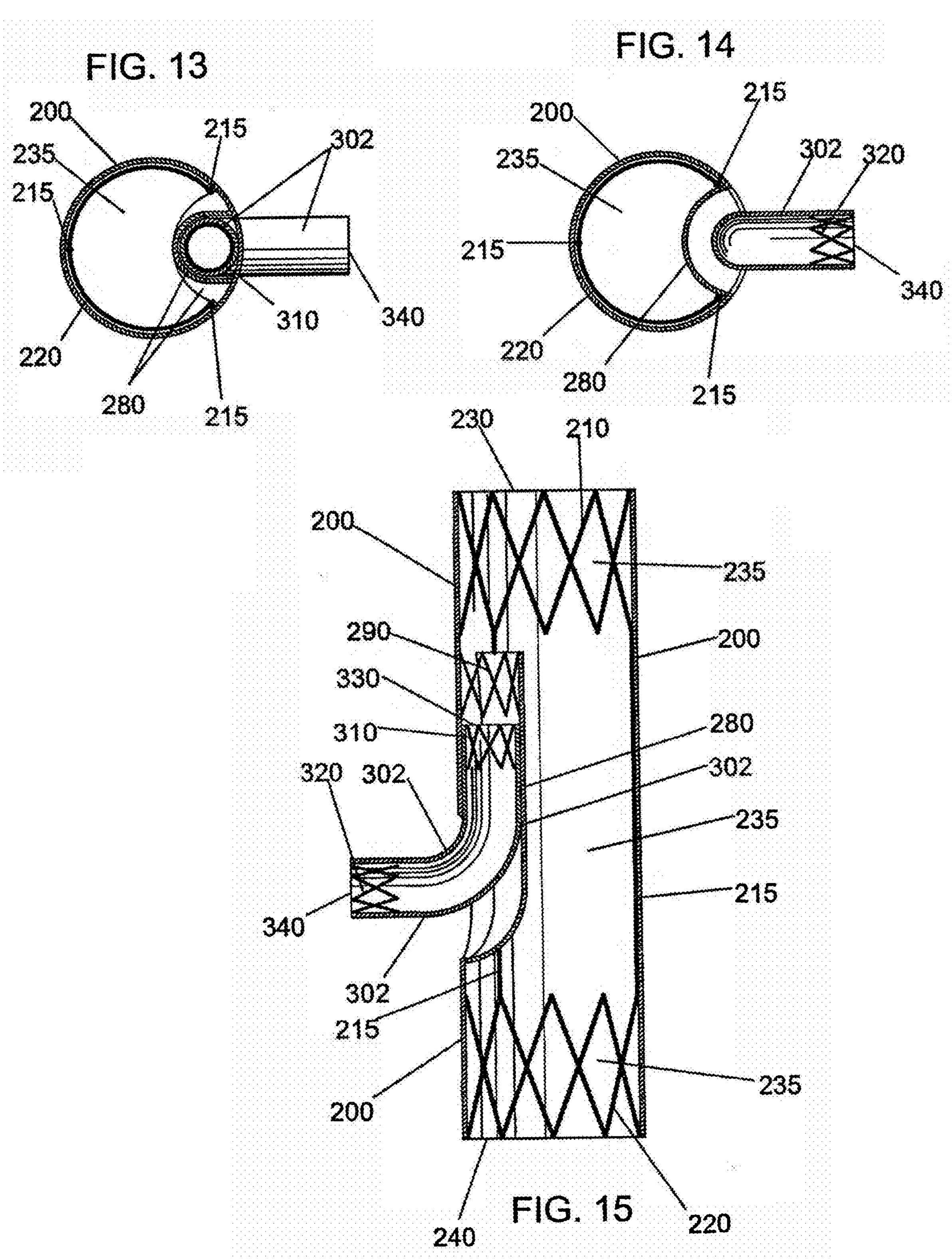
FIG. 13 shows a transverse-sectional view of a bifurcated stent graft according to the present invention.
FIG. 14 shows a transverse-sectional view of a bifurcated stent graft according to the present invention.
FIG. 15 shows a longitudinal-sectional view of a bifurcated stent graft according to the present invention.

The embodiments shown in the Figures are exemplary, and should not be construed as limiting the scope of the present invention as disclosed and/or claimed herein.

DETAILED DESCRIPTION OF THE ILLUSTRATED EMBODIMENTS

For purposes of the present written description and/or claims, "proximal" shall denote the direction along a vessel system in which multiple smaller vessels come together to form a larger vessel, and "distal" shall denote the opposite direction, i.e., the direction in which a larger vessel divides into multiple smaller vessels. For an arterial system proximal therefore corresponds to "upstream", while distal corresponds to "downstream". It should be noted that for a venous system or a lymphatic system, the correspondence would be reversed. The correspondence may vary for other vascular or duct systems.

A bifurcated intravascular primary stent graft 100 according to the present invention is illustrated in FIGS. 1-9 and comprises: a first primary stent segment 210; a second primary stent segment 220; a primary graft sleeve 200 having first open end 230, having a second open end 240, forming a main fluid flow channel 235 therebetween, and having a side opening 250 therethrough; and an internal graft channel 260 formed by partition 280 within the primary graft sleeve 200 and having an inner open end 270 within the primary graft sleeve 200 and an outer open end communicating with the side opening 250 of the primary graft sleeve 200. An internal stent segment 290 may be provided near the inner open end 270 of internal graft channel 260, to keep internal graft channel 260 open and to facilitate later deployment of a secondary stent graft (described herein below). The internal graft channel 260 and partition 280 thereby form at least a portion of a branch fluid flow channel between main channel 235 and the side opening 250 of the primary graft sleeve 200. Primary graft sleeve 200 may be operatively coupled near the first open end 230 to the first primary stent segment 210 and operatively coupled near the second open end 240 to the second primary stent segment 220, so that stent segments 210 and 220 and graft sleeve 200 thereby form a single operative unit. Each stent segment and the corresponding open end may preferably be adapted for engaging an endoluminal surface of a main vessel and forming a substantially fluid-tight seal therewith.

A bifurcated intravascular stent graft according to the present invention may comprise a primary stent graft 100 and may further comprise a secondary stent graft 300 as illustrated in FIGS. 10-15. The secondary stent graft 300 comprises: a first secondary stent segment 310; a second secondary stent segment 320; and a secondary graft sleeve 302. Secondary graft sleeve 302 may be operatively coupled near first open end 330 to the first secondary stent segment 310 and operatively coupled near second open end 340 to the second secondary stent segment 320, so that stent segments 310 and 320 and secondary graft sleeve 302 thereby form a single operative unit. Secondary stent 300 may be adapted to pass within internal graft channel 260 and through side opening 250. First stent segment 310 and corresponding first open end 330 may preferably be adapted for engaging an inner surface of internal graft channel 260 and forming a substantially fluid-tight seal therewith. Second stent segment 320 and corresponding second open end 340 may preferably be adapted for engaging an endoluminal surface of a branch vessel and forming a substantially fluid-tight seal therewith. Secondary stent graft 300 may therefore form at least a portion of the branch fluid flow channel.

The stent graft of the present invention is particularly well-suited for repair of main vessel segments where a branch vessel leaves the main vessel at an angle approaching 90°. Previous bifurcated stent graft devices enable repairs where a branch vessel leaves the main vessel at a substantially smaller angle of less than about 45°. This condition does not obtain at several potentially important vessel repair sites. Other previous devices enable repair at such high-angled branches only when transluminal access to a distal portion of the branch vessel is possible. In many instances such access is either impossible (celiac artery, mesenteric arteries, renal arteries) or extremely difficult and/or dangerous (carotid arteries). Still other previous devices do not provide a substantially fluid-tight seal with the branch vessel, thereby partially defeating the purpose of the stent graft (i.e., shielding the repaired portion of the main vessel and/or branch vessel from intravascular fluid pressure).

Figure 16:
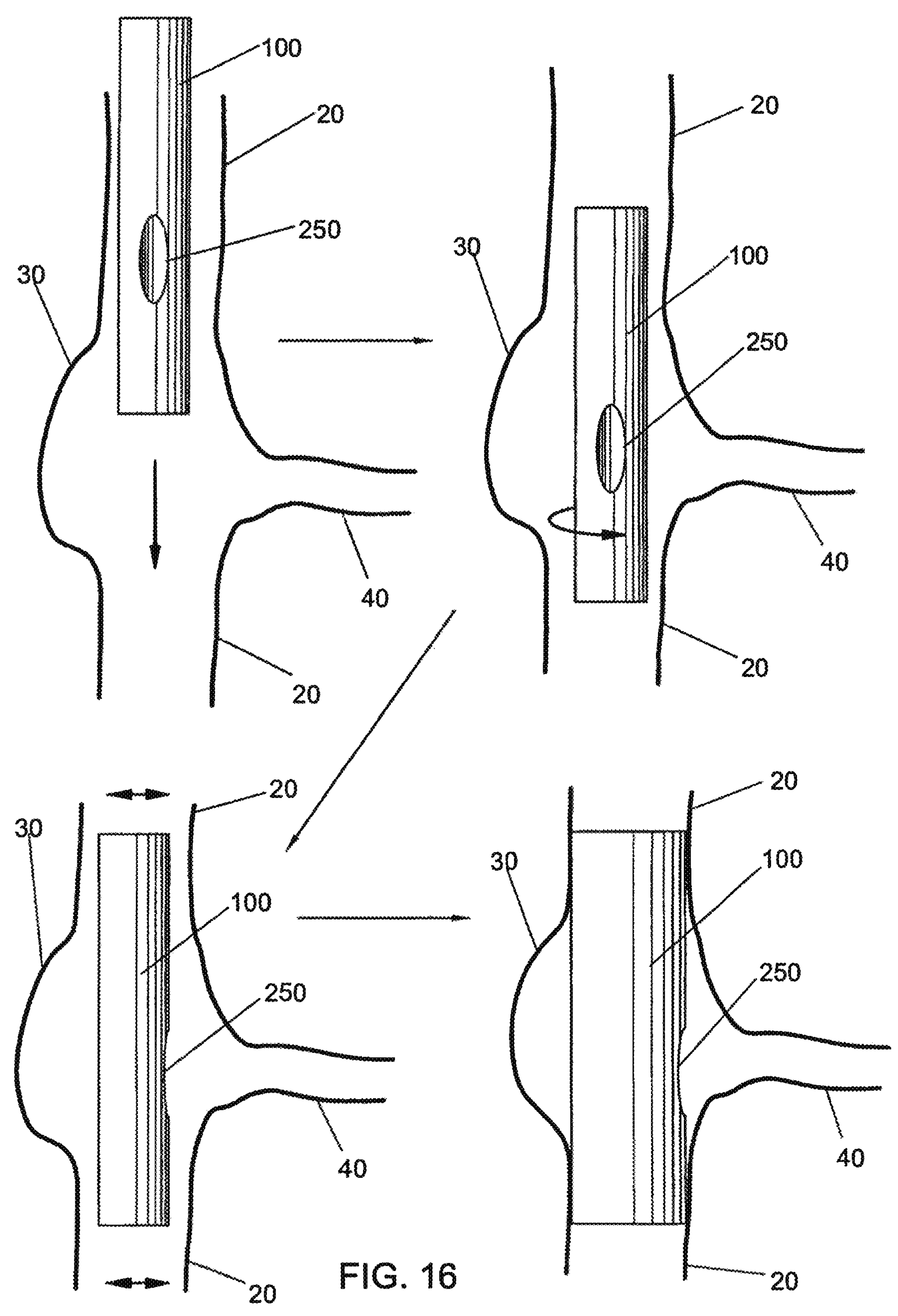
FIG. 16 shows a procedure for deploying a primary stent graft according to the present invention.

The stent graft of the present invention, in contrast, addresses these issues. As shown in FIGS. 16, bifurcated primary stent graft 100 may be delivered transluminally to a repair site 30 of a main vessel 20, and may be adjusted longitudinally and/or rotated about its long axis within the main vessel lumen until side opening 250 is substantially aligned with the lumen of branch vessel 40. Bifurcated primary stent graft 100 may be provided with one or more radiopaque markers or indexes to facilitate the alignment under fluoroscopic imaging. First primary stent segment 210 and first open end 230 may be engaged with the endoluminal surface of a first segment of the main vessel 20 near the repair site to form a substantially fluid-tight seal, and second primary stent segment 220 and second open end 240 may be engaged with the endoluminal surface of a second segment of the main vessel 20 near the repair site to form a substantially fluid-tight seal, thereby deploying bifurcated primary stent graft 100 within the repair site 30 of main vessel 20. Bifurcated primary stent graft 100 may be delivered through the main vessel from upstream or from downstream, as dictated by the particular clinical circumstances.

Figure 17:
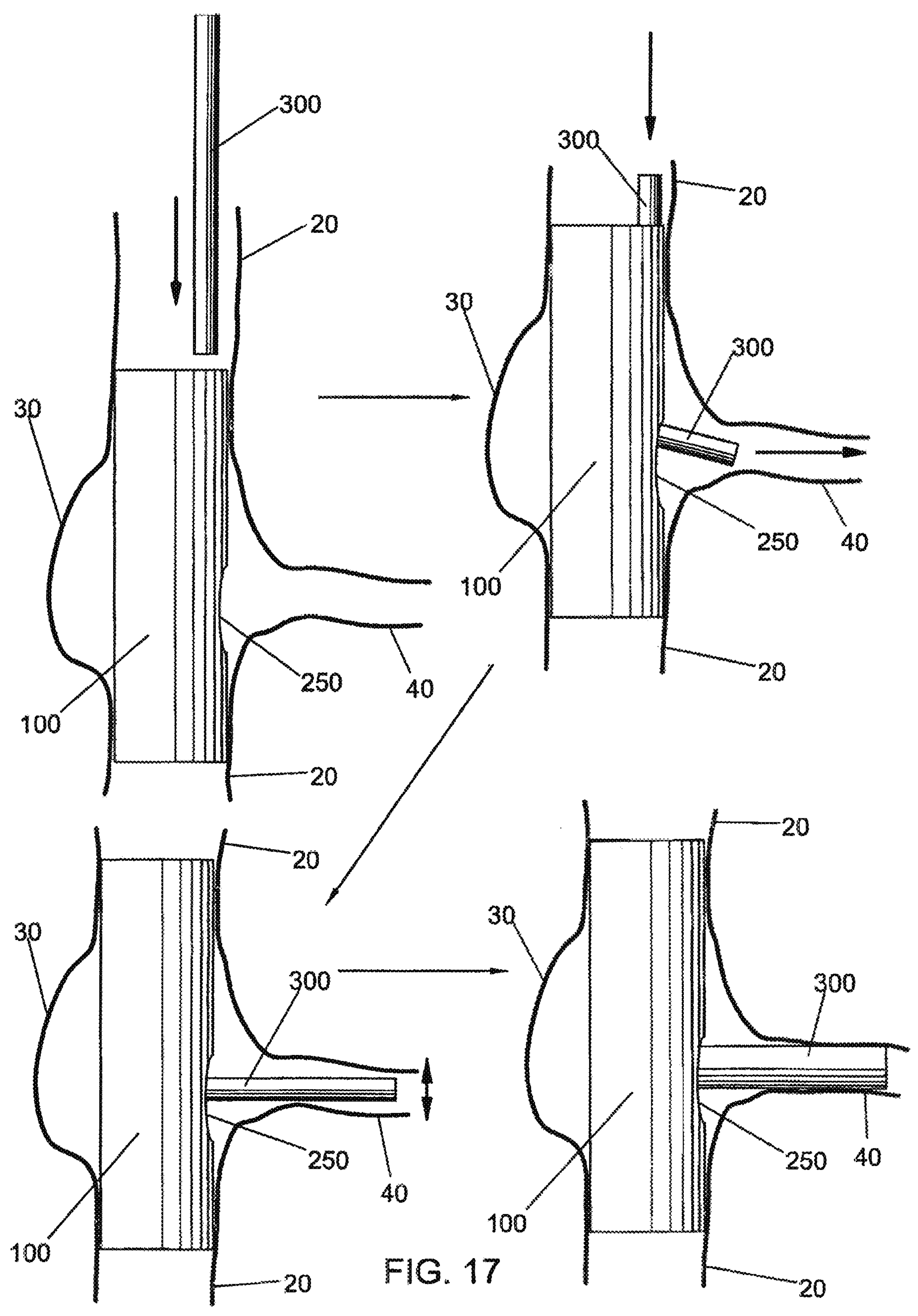
FIG. 17 shows a procedure for deploying a secondary stent graft according to the present invention.
Figures 18, 19, 20, 21, 22:
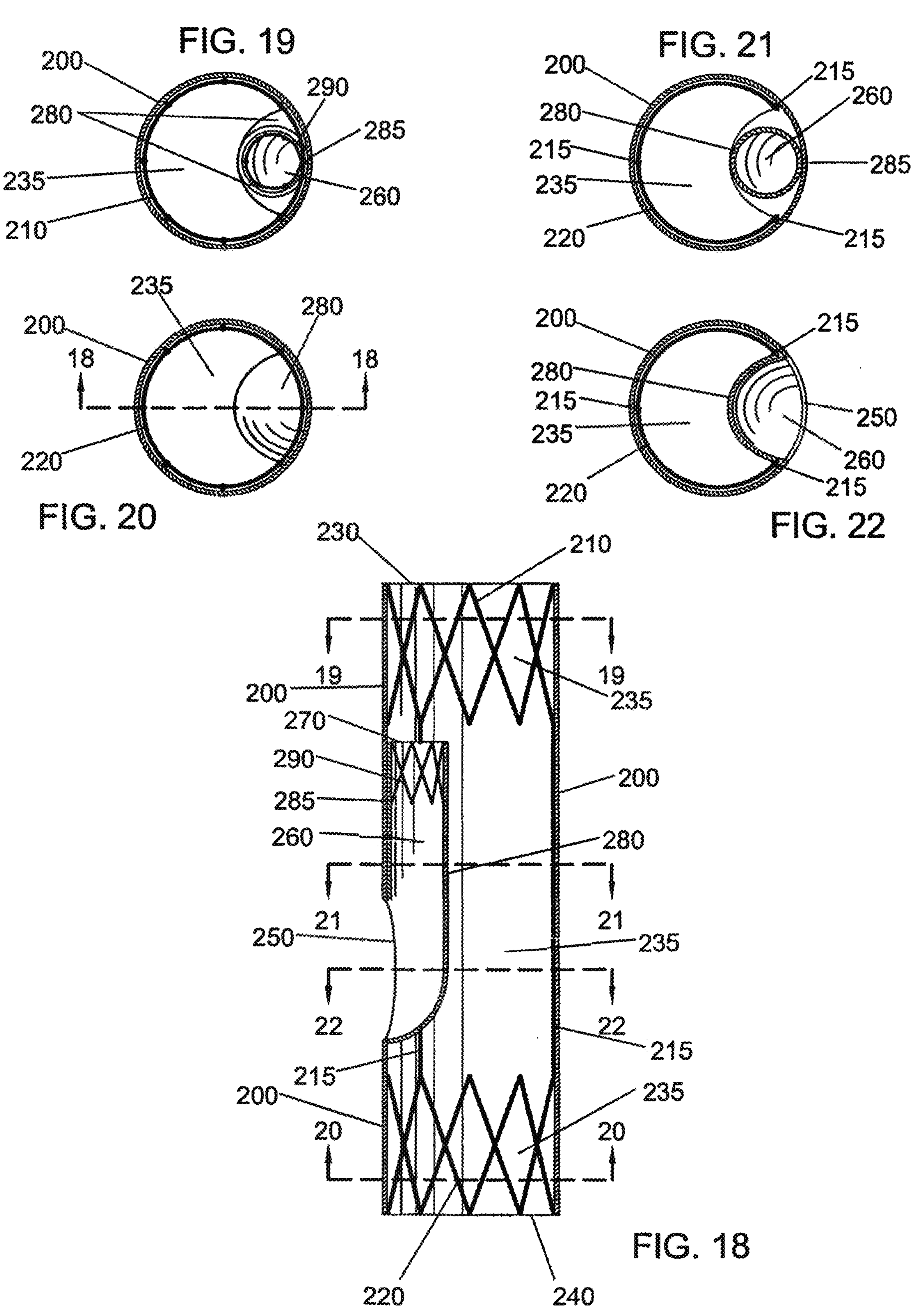
FIG. 18 shows a longitudinal-sectional view of a primary stent graft according to the present invention.
FIG. 19 shows a transverse-sectional view of a primary stent graft according to the present invention.
FIG. 20 shows a transverse-sectional view of a primary stent graft according to the present invention.
FIG. 21 shows a transverse-sectional view of a primary stent graft according to the present invention.
FIG. 22 shows a transverse-sectional view of a primary stent graft according to the present invention.

After delivery and deployment of bifurcated primary stent graft 100 at the repair site 30, secondary stent graft 300 is then delivered to the repair site and deployed, as illustrated in FIG. 17. Secondary stent graft 300 is delivered transluminally to the repair site and passed within internal graft channel 260 of primary stent graft 100. Secondary stent graft 300 may be delivered within the main vessel to the repair site from the same direction as primary stent graft 100, or from the opposite direction if feasible and/or desirable. Delivery from the same direction as delivery of primary stent graft 100 within the main vessel may be preferred due to the preferred construction of internal graft channel 260. Secondary stent graft 300 may also be delivered from a distal point within the branch vessel 40 if feasible and/or desirable. Secondary stent graft 300 is positioned at least partially within internal graft channel 260, passing through side opening 250 and into branch vessel 40. Secondary stent graft 300 may be provided with one or more radiopaque markers or indexes to facilitate the positioning under fluoroscopic imaging. First secondary stent segment 310 and first open end 330 may be engaged with the inner surface of the internal graft channel 260 to form a substantially fluid-tight seal, and second secondary stent segment 320 and second open end 340 may be engaged with the endoluminal surface of the branch vessel 40 to form a substantially fluid-tight seal, thereby deploying secondary stent graft 300 within the internal graft channel 260 and the branch vessel 40. When deployed together in this way, the first and second substantially fluid-tight seals of primary stent graft 100 and secondary stent graft 300 together substantially shield the main vessel walls and/or the branch vessel walls at the repair site from intravascular fluid pressure, while preserving fluid flow both through the main vessel and into the branch vessel.

Once deployed, incoming fluid flow (i.e., arterial or venous blood flow in the typical deployment scenario) may enter either open end 230 or 240 of bifurcated stent graft 100 and pass through main fluid flow channel 235. Upon reaching the inner open end 270 of internal graft channel 260, the incoming fluid flow divides into a portion continuing to flow in the main fluid flow channel 235 and a portion flowing through the branch fluid flow channel within internal graft channel 260 and through side opening 250. The fluid flow in main channel 235 continues out of bifurcated stent graft 100 and back into the main vessel 20. The branch fluid flow channel comprises a portion of internal graft channel 260 and the interior of secondary stent graft 300, and the branch fluid flow passes into the open inner end 270 of internal graft channel 260, into the open first end 330 of secondary stent graft 300, through secondary stent graft 300 (and therefore through side opening 250), out of open second end 340 of secondary stent graft 300, and into branch vessel 40. Stent graft 300 may preferably be made sufficiently flexible to be bent through angles ranging from about 0° through about 180° while still forming a portion of the branch fluid flow channel. In this way the bifurcated stent graft of the present invention may be used to repair main vessels near where branch vessels leave the main vessel at arbitrarily large angles, even approaching about 180°. To facilitate longitudinal and/or rotational alignment of bifurcated primary stent graft 100 relative to the lumen of the branch vessel, side opening 250 through primary graft sleeve 200 may be made substantially larger than the lumen, thereby increasing the range of positions of bifurcated primary stent graft 100 that nevertheless enable passing secondary stent graft 300 through side opening 250 and into branch vessel 40. It may be desirable for internal graft channel 260 to increase in size with distance from inner open end 270, so that the size of the open inner end of internal graft channel 260 may substantially match the size of secondary stent graft 300 and/or the lumen of branch vessel 40, while the outer open end of internal graft channel 260 may substantially match the relatively enlarged size of side opening 250.

Without departing from inventive concepts disclosed and/or claimed herein, any suitable configuration and/or materials (currently known or hereafter developed) may be employed for stent segments 210, 220, 290, 310, and/or 320. Many suitable configurations for intravascular stents have been developed over the years, as disclosed in the incorporated references and in references cited therein (U.S. Pat. Nos. 5,855,598 and 6,093,203 are of particular note for containing many examples). Such stent configurations may include but are not limited to braids (open-lattice or closely-woven), helical structural strands, sinusoidal structural strands, mesh-like materials, diamond-shaped mesh, rectangular shaped mesh, functional equivalents thereof, and/or combinations thereof. Materials should be sufficiently strong, bio-compatible, hemo9 compatible, corrosion-resistant, and fatigue-resistant, and may include metals, plastics, stainless steels, stainless spring steels, cobalt-containing alloys, titanium-containing alloys, nitinol, nickel-containing alloys, nickel-titanium alloys, composite materials, clad composite materials, other functionally equivalent materials (extant or hereafter developed), and/or combinations thereof. Whatever its construction, a stent graft may typically be delivered transluminally to a vascular repair site with the stent segment in a radially compressed configurations having a delivery diameter sufficiently small to pass through any required vessels to the repair site. Once positioned properly, the stent segment may be radially enlarged to a deployed diameter. The stent segment may be fabricated so that the delivery diameter is achieved through elastic radial compression of the stent segment (maintained during transluminal delivery by a sleeve or equivalent device). Once properly positioned, the sleeve or equivalent device may be removed, thereby allowing the stent segment to expand to its deployed diameter. The deployed diameter may be smaller than the uncompressed diameter of the stent segment, so that residual elastic expanding force exerted by the stent segment may serve to hold the vessel open, fix the stent in place in the vessel, and/or form a substantially fluid-tight seal with the endoluminal surface of the vessel (in conjunction with a graft sleeve). Alternatively, the stent segment may comprise material(s) that undergo plastic deformation. The stent graft may be delivered transluminally with the stent segment having a delivery diameter sufficiently small to allow delivery to the repair site. The stent segment may then be expanded (by an intra-luminal balloon catheter or other functionally equivalent device) to a deployed diameter, and may maintain the deployed diameter due to plastic deformation of the stent segment during expansion. The expanded stent segment may serve to engage the endoluminal surface of the vessel to hold the vessel open, hold the stent graft in position, and/or form a substantially fluid-tight seal with the vessel. Other methods of delivery and/or deployment may be employed without departing from inventive concepts disclosed and/or claimed herein.

Whatever configuration of stent segment(s) is employed, the stent segment must be adapted to engage the endoluminal surface of the vessel. This may be accomplished by any suitable method (currently known or hereafter developed; for example as disclosed in the incorporated references and in references cited therein), including but not limited to: elastic or plastic expansion; sutures; ligatures; clips; barbs; endoluminal cellular overgrowth; functional equivalents thereof; and/or combinations thereof.

Figures 32, 33, 34:
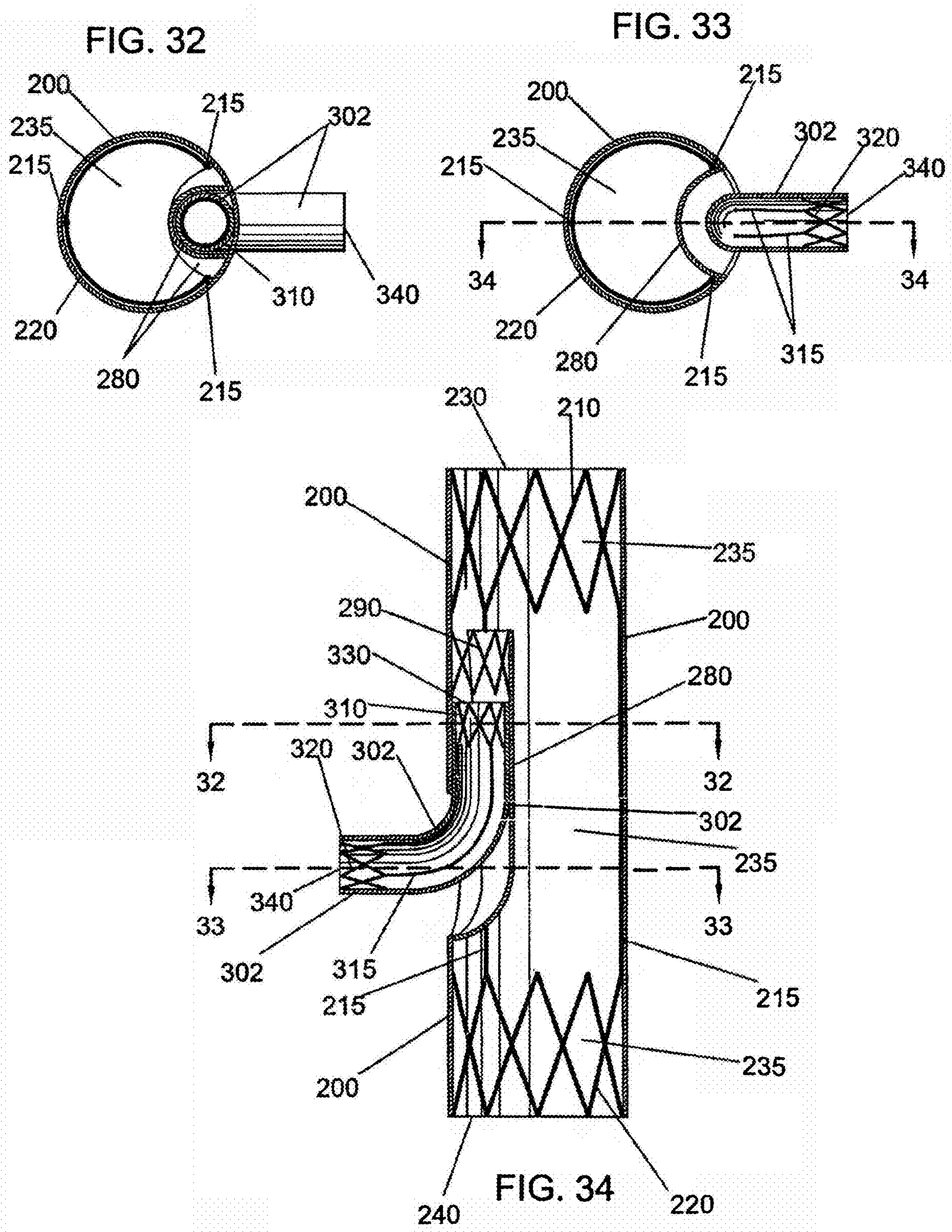
FIG. 32 shows a transverse-sectional view of a bifurcated stent graft according to the present invention.
FIG. 33 shows a transverse-sectional view of a bifurcated stent graft according to the present invention.
FIG. 34 shows a longitudinal-sectional view of a bifurcated stent graft according to the present invention.

First and second stent segments corresponding to a single graft sleeve of a single stent graft have been shown herein as separate structural elements. Pairs of first and second stent segments (segments 210 and 220, for example, or 310 and 320) may be mechanically connected by a stent coupling member. Three longitudinal wires 215 are shown serving to connect stent segments 210 and 220 of primary stent graft 100, while longitudinal wires 315 are shown serving to connect stent segments 310 and 320 in FIGS. 32, 33, and 34. Other functionally equivalent configurations may be employed without departing from inventive concepts disclosed and/or claimed herein. In particular, it may be desirable for corresponding first and second stent segments to comprise first and second ends of a single stent. In the case of stent segments 210 and 220, a single primary stent would require a side opening corresponding to side opening 250 of graft sleeve 200. No such side opening would be required for a single secondary stent comprising first and second segments 310 and 320. Such a single stent may be preferred for secondary stent graft 300, since it is typically bent to enter a branch vessel but must nevertheless maintain an open branch fluid channel.

Without departing from inventive concepts disclosed and/or claimed herein, any suitable configuration and/or materials (currently known or hereafter developed) may be employed for primary graft sleeve 200, partition 280, and/or graft sleeve 300. Such sleeve materials may include, but are not limited to: continuous sheets; interwoven textile strands; multiple filament yarns (twisted or un-twisted); monofilament yarns; PET (Dacron), polypropylene, polyethylene, high-density polyethylene, polyurethane, silicone, PTFE, polyolefins, ePTFE, biologically-derived membranes (such as swine intestinal submucosa), functional equivalents thereof, and/or combinations thereof. The graft sleeve may be delivered at the size appropriate for deployment at the repair site, or may be a smaller size and stretched (plastically deformed) at the repair site to the desired deployed size. Graft sleeves are shown herein outside the corresponding stent segment, but the stent segment may equivalently be outside the corresponding graft sleeve. The graft sleeve and corresponding stent segment(s) may be operatively coupled by any suitable method (currently known or hereafter developed), including but not limited to: sutures, ligatures, clips, barbs, adhesives (silicone, siloxane polymer, fluorosilicones, polycarbonate urethanes, functional equivalent thereof, and/or combinations thereof); functional equivalent thereof, and/or combinations thereof. Alternatively, a graft sleeve and corresponding stent segment(s) may comprise a single integral structure. Without departing from inventive concepts disclosed and/or claimed herein, an end of a graft sleeve and the corresponding stent segment may extend longitudinally substantially equally (as shown in the Figures), the graft sleeve may extend longitudinally beyond the stent segment, or the stent segment may extend longitudinally beyond the graft sleeve. Without departing from inventive concepts disclosed and/or claimed herein, a graft sleeve may be adapted to engage an endoluminal vessel surface by endoluminal cellular invasion (by manipulation of graft sleeve porosity or other equivalent technique), thereby substantially fixing the graft sleeve to the vessel and forming a substantially fluid-tight seal therewith.

In the present invention, a substantially fluid-tight seal between a stent graft and a vessel may be achieved by adapting the graft sleeve and corresponding stent segment to engage the endoluminal surface of the vessel. This may be readily achieved by using a graft sleeve outside the stent segment. Expansion of the stent segment (either elastic or plastic) may then serve to press the graft sleeve against the inner vessel surface, thereby forming the substantially fluid-tight seal. For a graft sleeve inside the stent segment, a substantially fluid-tight connection between the stent segment and the graft sleeve is required, thereby resulting in a substantially fluid-tight seal between the graft sleeve and vessel surface when the stent segment engages the vessel surface. Without departing from inventive concepts disclosed and/or claimed herein, many other functionally equivalent configurations (currently known or hereafter developed) may be contrived for operatively coupling a graft sleeve to a stent segment, and for engaging an endoluminal surface of the vessel and forming a substantially fluid-tight seal therewith.

Figures 23, 24, 25, 28, 29, 30, 31:
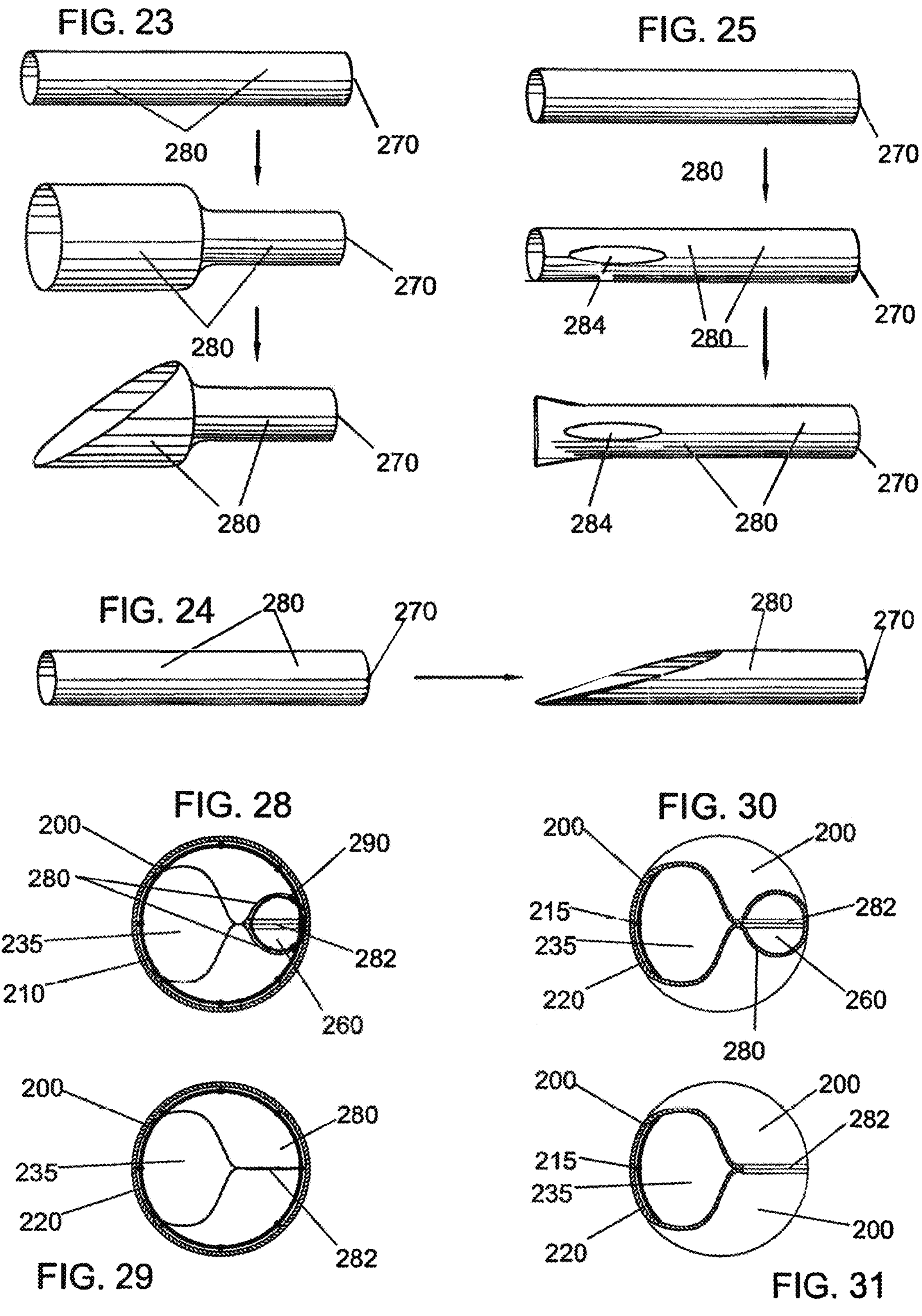
FIG. 23 shows a procedure for adapting an internal graft sleeve according to the present invention.
FIG. 24 shows a procedure for adapting an internal graft sleeve according to the present invention.
FIG. 25 shows a transverse-sectional view of a primary stent graft according to the present invention.
FIG. 28 shows a transverse-sectional view of a bifurcated stent graft according to the present invention.
FIG. 29 shows a transverse-sectional view of a bifurcated stent graft according to the present invention.
FIG. 30 shows a transverse-sectional view of a bifurcated stent graft according to the present invention.
FIG. 31 shows a transverse-sectional view of a bifurcated stent graft according to the present invention.
Figures 26, 27:
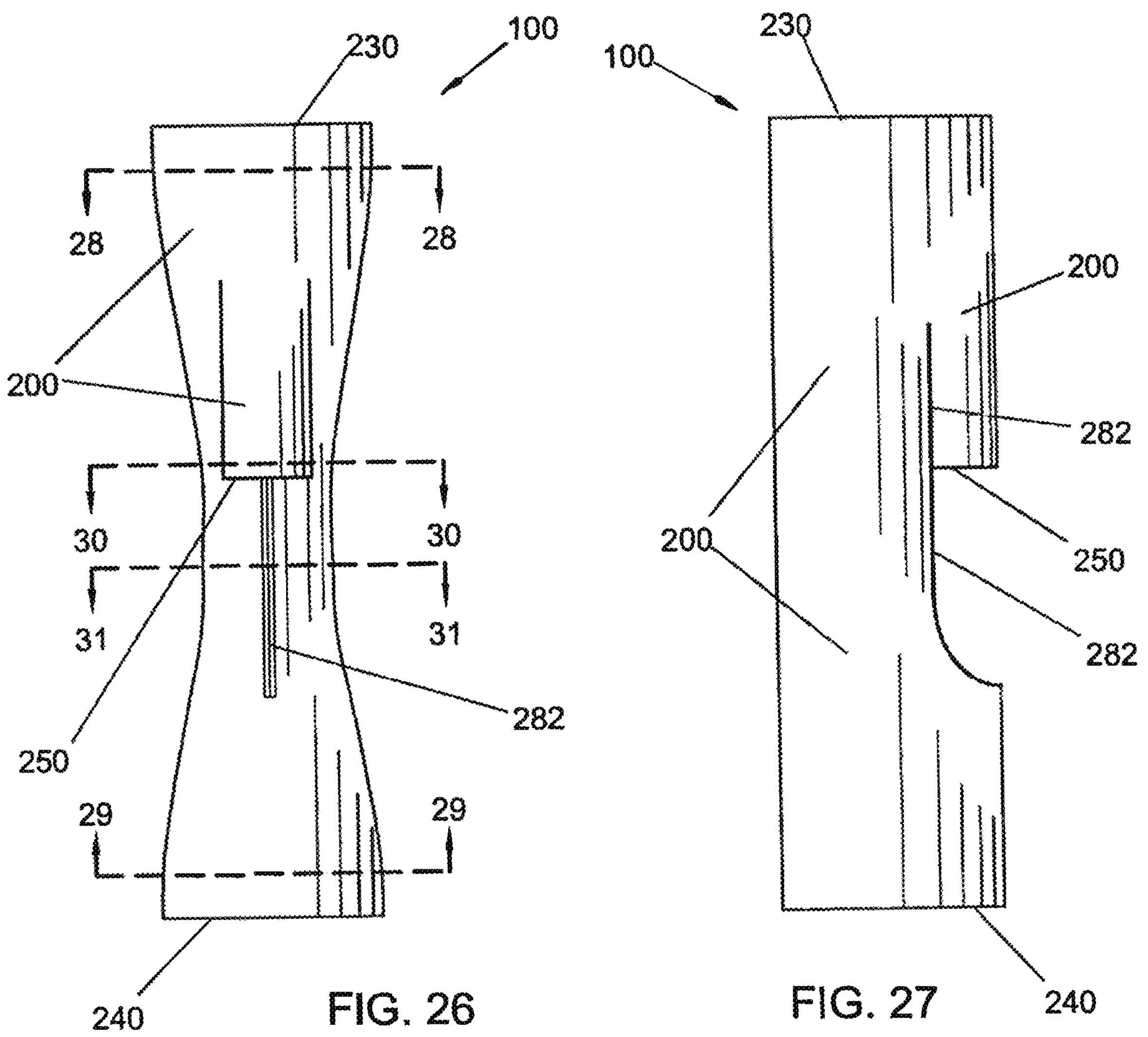
FIG. 26 shows a front view of a bifurcated stent graft according to the present invention.
FIG. 27 shows a side view of a bifurcated stent graft according to the present invention.

Internal graft channel 260 and partition 280 may be formed in a variety of functionally equivalent ways without departing from inventive concepts disclosed and/or claimed herein. As shown in FIGS. 1-15, internal graft channel 260 may be formed by securing an elongated sheet of graft sleeve material to the inner surface of graft sleeve 200 with substantially fluid-tight seams along each side edge of the sheet and along one end of the sheet, with the sheet serving as partition 280. Alternatively, an internal graft sleeve having open inner and outer ends may be secured longitudinally to the inner surface of graft sleeve 200 (FIGS. 18-22). The internal graft sleeve may be secured along one or more longitudinal seams 285, and/or at one or more discrete contact points. The open inner end 270 of the internal sleeve may preferably be secured to the inner surface of graft sleeve 200 while remaining open, thereby facilitating subsequent insertion of secondary stent graft 300 thereinto. The sides of the internal graft sleeve serve as partition 280. The outer open end of the internal graft sleeve may be secured around its perimeter to side opening 250 of graft sleeve 200 to form a substantially fluid-tight seal. The outer end of the internal graft sleeve may be adapted to facilitate communicating with and securing to side opening 250 in a variety of ways, including but not limited to: enlarging the outer end of the internal graft sleeve (FIG. 23); providing the outer end with a diagonal opening (FIGS. 23 and 24); providing the internal graft sleeve with a side opening 284 near the outer end thereof (the outer end itself would then preferably be closed; FIG. 25); functionally equivalent methods; and/or combinations thereof. Seams and/or contact points for securing two graft sleeves together and/or securing a sheet of graft sleeve material to a graft sleeve and may be accomplished by any suitable technique (extant or hereafter developed), including but not limited to: sutures, ligatures, clips, other fasteners, fusion bonding, electronic welding, thermal bonding, thermal welding, chemical welding, adhesives, functional equivalents thereof, and/or combinations thereof.

FIGS. 26-31 illustrate an embodiment of primary stent graft 100 in which the internal primary graft channel 260 is formed by securing together, along a substantially longitudinal seam 282, portions of an inner surface of the primary graft sleeve 200 separated by a circumferential seam spacing. The first end of the seam 282 extends toward the first end 230 of the primary graft sleeve 200 beyond the side opening 250, while the second end of the seam 282 extends toward the second end 240 of the primary graft sleeve 200 beyond the side opening 250. The circumferential seam spacing decreases to substantially zero at the second end of the seam, and the side opening 250 lies within the circumferential seam spacing. In this way a single graft sleeve 200 may be used to provide both main and branch fluid flow channels, thereby simplifying manufacture of the bifurcated stent graft. Secondary stent graft 300 may be inserted through internal primary graft channel 260, out through side opening 250, and into the branch vessel in substantially the same manner as described hereinabove.

FIGS. 35-41 illustrate an embodiment of a bifurcated stent graft in which multiple side openings 250 are provided in the primary graft sleeve 200, each as a circumferential slit in the graft sleeve. A portion of the graft sleeve adjacent the slit is pushed inward, producing an opening. An external primary graft channel 262 is formed by securing (by suturing, thermal bonding, or other suitable techniques) additional graft material to the outer surface of the primary graft sleeve 200. The additional graft material may take the form of a sleeve 200 the exterior of the primary graft sleeve 200 (as shown in FIGS. 35-41), or may be provided by securing a strip of graft material along its side edges to the exterior of the primary graft sleeve 200, forming the external primary graft channel 262 between the strip and the primary graft sleeve 200. In either case, the external graft channel 262 thus formed communicates with interior of the primary graft sleeve 200 (i.e., with the primary graft channel 235) through the opening 250 in the primary graft sleeve 200, and provides a fluid flow channel 252 between the primary graft channel 235 through the primary graft sleeve 200. Three such external primary graft channels 262 are shown in the Figures at varying longitudinal and circumferential positions. This exemplary arrangement might be suitable for a stent graft in the abdominal aorta spanning the branch points of the renal arteries and superior mesenteric arteries, for example. Other numbers and/or arrangements of the external primary graft channels may be employed that may be suitable for other stent graft locations while remaining within the scope of the present invention. This embodiment may be more readily fabricated than others since all seams may be made on the exterior surface of the primary graft sleeve.

Figures 35, 36:
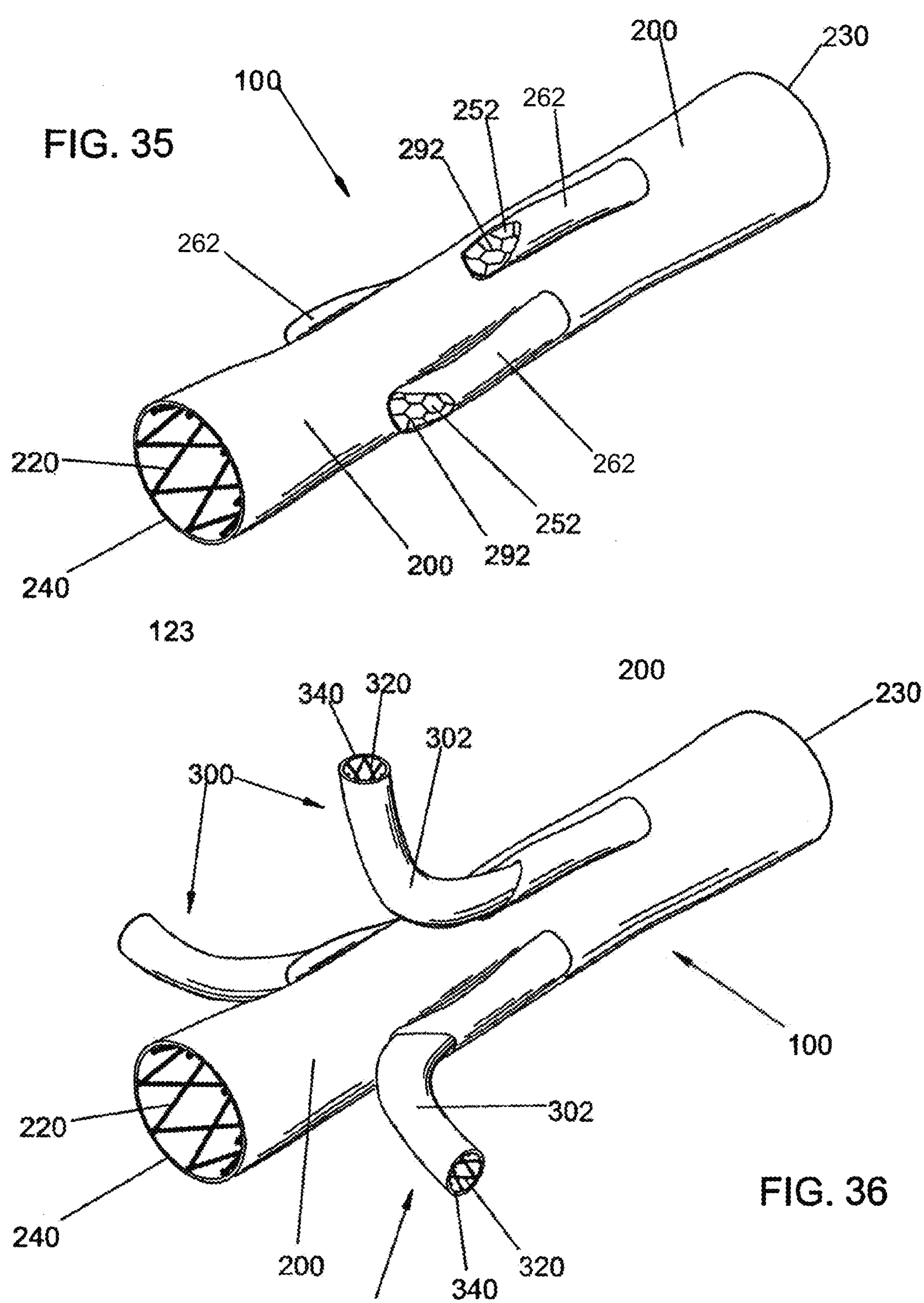
FIG. 35 shows an isometric view of a primary stent graft according to the present invention.
FIG. 36 shows an isometric view of a bifurcated stent graft according to the present invention.
Figures 38, 39, 40:
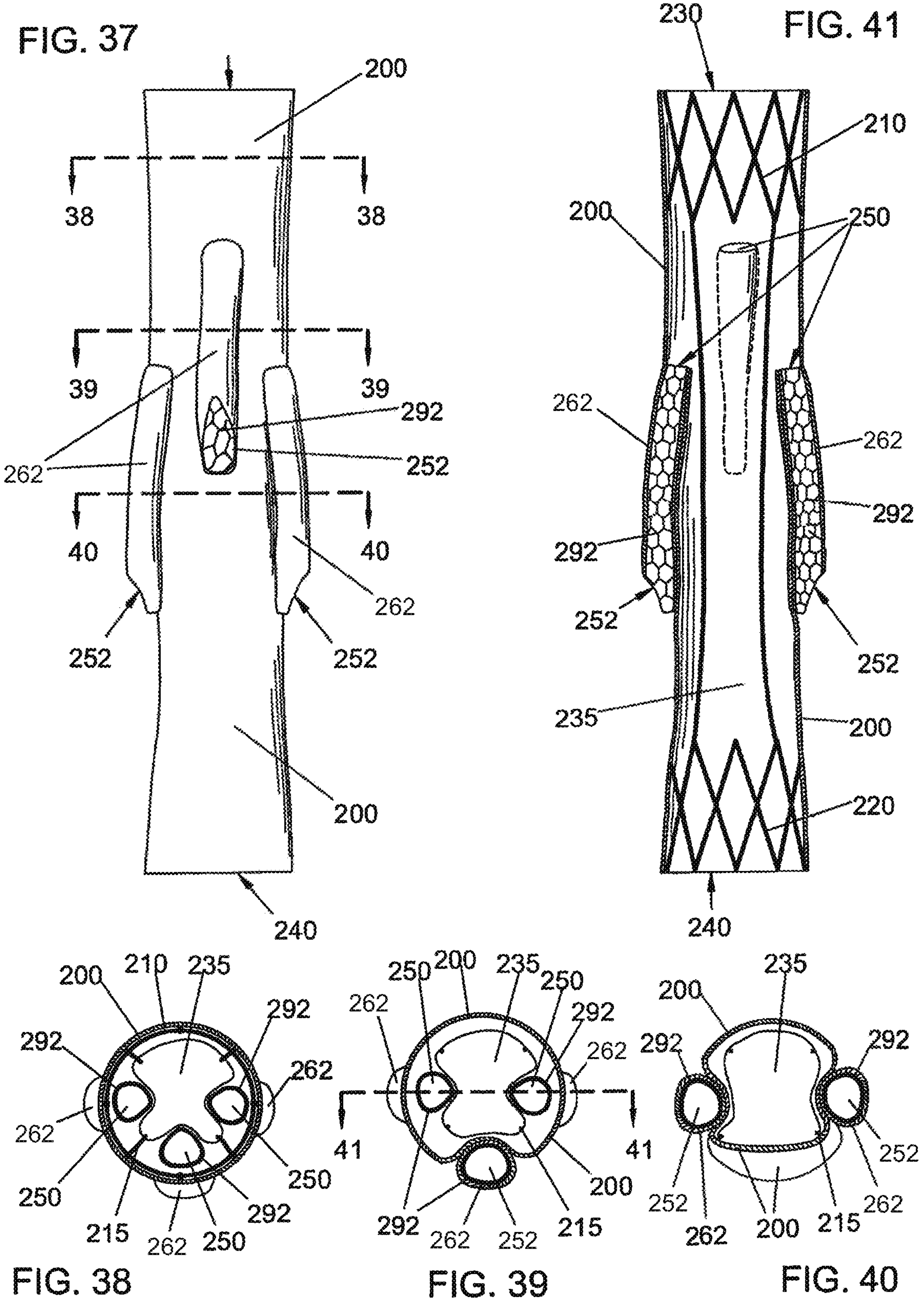
FIG. 38 shows a transverse-sectional view of a primary stent graft according to the present invention.
FIG. 39 shows a transverse-sectional view of a primary stent graft according to the present invention.
FIG. 40 shows a transverse-sectional view of a primary stent graft according to the present invention.

The primary graft sleeve 200 shown in FIGS. 35-41 may be provided with stent segments 210/220 near the ends 230/240 thereof and with stent coupling members 215 as disclosed hereinabove. Each external primary graft channel 262 is shown with a stent segment 292 for providing structural support and for keeping the opening 250 through the primary graft sleeve 200 open. A hexagonal wire mesh extending along substantially the entire length of the external primary graft channel is shown, but other stent configurations may be equivalently employed (including separate first and second stent segments positioned within the external primary graft channel near the ends thereof, a single stent segment within the external primary graft channel near the primary graft sleeve opening, or other suitable arrangements). In FIG. 36, the primary stent graft 100 is shown with a secondary stent graft 300 positioned in and extending from each of the external primary graft channels 262. The secondary stent grafts 300 may preferably include a secondary graft sleeve 302 and secondary stent segments 310/320 within the secondary graft sleeve 302 near the ends thereof. The stent segments 310/320 may be separate (as in FIG. 15), may be connected by stent segment coupling members 315 (as in FIG. 34), or may comprise the ends of a single stent extending substantially the entire length of the secondary graft sleeve 302 (not shown). When deployed (as in FIG. 16), the primary stent graft 100 of FIG. 35 may form substantially fluid-tight seals with an endoluminal surface of a vessel near the ends of the primary stent graft, by engagement of the stent segments 210/220 with the vessel. The primary stent graft 100 may therefore span a damaged portion of the vessel (including any branch points). The side opening(s) 250 and external primary graft channel(s) 262 therefore communicate with a fluid volume that is substantially isolated from intravascular volumes both upstream and downstream of the primary stent graft. One or more secondary stent grafts 300 may be deployed through corresponding side opening(s) 250, into corresponding external primary graft channel(s) 262, and into corresponding branch vessel(s) (as in FIG. 17). The proximal end 330 of a secondary stent graft 300 thus deployed forms a substantially fluid-tight seal within the corresponding external primary graft channel 262, while the distal end 340 forms a substantially fluid-tight seal within the branch vessel. A blood flow channel is thereby provided from the primary graft channel 235 into the AAHbranch vessel, while substantially isolating the damaged portion of the vessel (including the branch point) from intravascular fluid pressure.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A stent graft comprising:

a primary stent construct;

a primary graft having a longitudinal axis and coupled to the primary stent construct, the primary graft extending between a first end and a second end and defining a length therebetween, the primary graft having an outer surface and an inner surface, the inner surface of the primary graft defining a primary fluid flow channel between the first end and the second end, the primary graft having a plurality of side openings into the primary fluid flow channel between the first end and the second end, wherein the plurality of side openings are each defined by an inwardly extending portion of the primary graft that extends inwardly relative to a remainder of the primary graft with the inwardly extending portion of the primary graft being longitudinally adjacent one of a plurality of circumferential slits formed in the primary graft such that the plurality of circumferential slits each form a respective one of the plurality of side openings with each one of the plurality of side openings facing in a longitudinal direction along the primary graft, the primary graft having a plurality of external graft channels coupled to an exterior surface of the primary graft at a respective one of the inwardly extending portions corresponding to the plurality side openings and being in fluid communication with a respective one of the plurality of side openings, wherein the primary fluid flow channel and each external graft channel of the plurality of external graft channels defines an open end oriented in the longitudinal direction, each external graft channel having an associated stent support configured to maintain the external graft channel in an open configuration; and a plurality of secondary grafts configured to be received within the plurality of external graft channels, each of the plurality of the secondary grafts including an end that opens in a same direction as the first end or the second end of the primary graft, each end of the plurality of secondary grafts having a branch fluid flow channel fluidly coupled to the primary fluid flow channel of the primary graft member through the respective side opening of the plurality of side openings in the primary graft.

2. The stent graft of claim 1, wherein each of the plurality of external graft channels defines an external fluid flow channel communicating with the primary fluid flow channel through the respective side opening in the primary graft.

3. The stent graft of claim 1, wherein each of the plurality of stent supports being coupled to a respective external graft channel of the plurality of external graft channels to maintain patency of each of the plurality of external graft channels.

4. The stent graft of claim 3, wherein each of the stent supports extends along each of the plurality external graft channels.

5. The stent graft of claim 1, wherein each of the plurality of external graft channels defines a raised surface relative to the outer surface of the primary graft.

6. The stent graft of claim 1, wherein the plurality of secondary grafts comprises a first secondary graft, a second secondary graft, and a third secondary graft.

7. The stent graft of claim 6, wherein each the first, second and third secondary grafts are spaced apart from one another circumferentially about the outer surface of the primary graft.

8. The stent graft of claim 1, where each of the plurality of secondary grafts form a fluid-tight seal with the plurality of external graft channels of the primary graft.

9. The stent graft of claim 1, wherein the primary graft defines at least three external graft channels to each receive a separate secondary graft therein.

10. A stent graft comprising:

a primary stent graft having a first end and a second end forming a primary fluid flow channel, the primary stent graft defining a first side opening and a second side opening between the first and second end, wherein a portion of the primary graft extends inward relative to a remainer of the primary graft to define the first and second side openings and the portion of the primary graft that extends inward is longitudinally adjacent to a respective first and second circumferential slit formed in the primary stent graft such that each of the respective first and second circumferential slits forms the respective first and second side openings and the first and second side openings face in a longitudinal direction corresponding to the longitudinal axis of the primary graft; and at least two external graft channels extending from respective first and second side openings on a first graft channel end and terminating in an opening oriented in the longitudinal direction on a second graft channel end, the at least two external graft channels formed by graft material coupled to an outer surface of the primary stent graft, each of the at least two external graft channels being spaced apart from one another circumferentially about the outer surface of the primary stent graft and configured to communicate with the primary fluid flow channel through the corresponding side opening in the primary stent graft, the at least two external graft channels each including a support configured to maintain the at least two external graft channels in an open configuration, the at least two external graft channels configured to each receive a branch member and connect the branch member to the primary fluid flow channel through the first and second sides openings, respectively, in the primary stent graft.

11. The stent graft of claim 10, wherein the at least two external graft channels each form an external fluid flow channel that includes at least portion of each of the external fluid flow channels that extend along the outer surface of the primary stent graft.

12. The stent graft of claim 11, wherein the at least two external fluid flow channels are arranged at different longitudinal and circumferential positions along the outer surface of the primary stent graft.

13. The stent graft of claim 10, wherein each support is a stent arranged at or adjacent to an end of the external graft channels.

14. The stent graft of claim 10, wherein an outer surface of each of the external graft channels extend outwardly from a circumference of the primary stent graft.

15. An endoprosthesis comprising:

a primary graft having a longitudinal axis and being coupled to a first stent at a first end of the primary graft and a second stent arranged at a second end of the primary graft, the primary graft having an outer surface configured to engage a vessel wall and an inner surface configured to define a primary fluid flow lumen between the first end and the second end, the primary graft having a first side opening and a second side opening into the primary flow lumen between the first end and the second end by a portion of the primary graft extended inwardly at each of the first and second side openings relative to a remainer of the primary graft and adjacent first and second circumferential slits such that the first and second side openings each face in a longitudinal direction along the primary graft and is along a length of the primary graft; and at least two external graft channels including a first external graft channel and a second external graft channel extending along the outer surface of the primary graft, the first external graft channel defined by a first graft member and the second external graft channel defined by a second graft member, wherein the first graft member has a first stent portion configured to support the first graft member in an open position and the second graft member has a second stent portion configured to support the second graft member in an open position, wherein the first graft member and second graft member define at least two external fluid flow channels communicating with the primary fluid flow channel through the respective first and second side openings in the primary graft, the at least two external graft channels extending substantially in a same longitudinal direction as the primary flow lumen, the at least two external graft channels each including an end opening in a same direction with the first end or the second end of the primary graft; and a first branch member having a branch fluid flow channel configured to engage an end section of the first external graft channel when the first external graft channel is in the open position and to connect the branch fluid flow channel of the first branch member to the primary fluid flow channel of the primary graft member through at least one of the first and second side openings in the primary graft.

16. The endoprosthesis of claim 15, comprising a second branch member having a branch fluid flow channel configured to engage an end section of the second external graft channel when the second external graft channel is in the open position and to connect the branch fluid flow channel of the second branch member to the primary fluid flow channel of the primary graft member through the other of the first and second side openings in the primary graft.

17. The endoprosthesis of claim 16, wherein the first branch member is configured to extend within the first external graft channel and second branch member is configured to extend within the second external graft channel.

18. The endoprosthesis of claim 16, wherein the first branch member is configured to engage with the end section of the first external graft channel in a fluid tight arrangement and the second branch member is configured to engage with the end section of the second external graft channel in a fluid tight arrangement.

19. The endoprosthesis of claim 15, wherein the primary graft is configured to substantially isolate a damaged portion of the aorta from intravascular fluid pressure and the first branch member is configured to allow blood flow to a branch vessel.

20. A branched prosthesis comprising:

a tubular graft body having a proximal end, a distal end, an inner lumen, a sidewall, and a longitudinal axis from the proximal end to the distal end;

a first fenestration in the sidewall formed by a first inwardly extending portion of the tubular graft body adjacent a first circumferential slit in the sidewall;

a second fenestration in the sidewall formed by a second inwardly extending portion of the tubular graft body adjacent a second circumferential slit in the sidewall;

a third fenestration in the sidewall formed by a third inwardly extending portion of the tubular graft body adjacent a third circumferential slit in the sidewall;

a first external graft channel connected to and extending longitudinally from the first fenestration and having an inner lumen in fluid communication with the first fenestration and a distally extending open end facing in a longitudinal direction corresponding to the longitudinal axis of the tubular graft body, the first external graft channel disposed along the sidewall at the first inwardly extending portion and configured to permit antegrade flow therethrough, and the first external graft channel supported by a first stent segment arranged toward the distally extending open end;

a second external graft channel connected to and extending longitudinally from the second fenestration and having an inner lumen in fluid communication with the second fenestration and a distally extending open end facing in the longitudinal direction, the second external graft channel disposed along the sidewall at the second inwardly extending depressed portion and configured to permit antegrade flow therethrough, and the second external graft channel supported by a second stent segment arranged toward the distally extending open end; and a third external graft channel connected to and extending longitudinally from the third fenestration and having an inner lumen in fluid communication with the third fenestration and a distally extending open end facing in the longitudinal direction, the third external graft channel disposed along the sidewall at the third inwardly extending portion and configured to permit antegrade flow therethrough, and the third external graft channel supported by a third stent segment arranged toward the distally extending open end.

* * * * *